United States Patent
Peyman

(10) Patent No.: US 10,376,600 B2
(45) Date of Patent: Aug. 13, 2019

(54) EARLY DISEASE DETECTION AND THERAPY

(71) Applicant: Gholam A. Peyman, Sun City, AZ (US)

(72) Inventor: Gholam A. Peyman, Sun City, AZ (US)

( * ) Notice: Subject to any disclaimer, the term of this patent is extended or adjusted under 35 U.S.C. 154(b) by 0 days.

(21) Appl. No.: 15/073,845

(22) Filed: Mar. 18, 2016

(65) Prior Publication Data

US 2017/0252466 A1 Sep. 7, 2017

Related U.S. Application Data

(60) Provisional application No. 62/303,219, filed on Mar. 3, 2016.

(51) Int. Cl.
| | | |
|---|---|---|
| A61K 49/22 | (2006.01) | |
| A61K 47/69 | (2017.01) | |
| A61K 47/68 | (2017.01) | |
| A61K 41/00 | (2006.01) | |
| A61K 49/00 | (2006.01) | |
| A61K 45/06 | (2006.01) | |

(52) U.S. Cl.
CPC ........ *A61K 49/221* (2013.01); *A61K 41/0028* (2013.01); *A61K 41/0057* (2013.01); *A61K 45/06* (2013.01); *A61K 47/68* (2017.08); *A61K 47/6923* (2017.08); *A61K 47/6929* (2017.08); *A61K 49/0058* (2013.01); *A61K 49/0067* (2013.01); *A61K 49/225* (2013.01)

(58) Field of Classification Search
None
See application file for complete search history.

(56) References Cited

U.S. PATENT DOCUMENTS

| | | | |
|---|---|---|---|
| 3,993,754 A | 11/1976 | Rahman et al. | |
| 4,235,871 A | 11/1980 | Papahadjopoulos et al. | |
| 4,522,803 A | 6/1985 | Lenk et al. | |
| 4,586,512 A | 5/1986 | Do-huu et al. | |
| 4,620,546 A | 11/1986 | Aida et al. | |
| 4,658,828 A | 4/1987 | Dory | |
| 4,891,043 A | 1/1990 | Zeimer et al. | |
| 5,094,854 A | 3/1992 | Ogawa et al. | |
| 5,118,666 A | 6/1992 | Habener | |
| 5,149,319 A | 9/1992 | Unger | |
| 5,203,782 A | 4/1993 | Gudov et al. | |
| 5,220,181 A | 6/1993 | Kanal et al. | |
| 5,545,618 A | 8/1996 | Buckley et al. | |
| 5,935,942 A | 8/1999 | Zeimer | |
| 5,976,502 A | 11/1999 | Khoobehi et al. | |
| 6,179,767 B1 | 1/2001 | Ziegler et al. | |
| 6,197,022 B1 | 3/2001 | Baker | |
| 6,248,727 B1 | 6/2001 | Zeimer | |
| 6,552,053 B2 | 4/2003 | Sun et al. | |
| 6,566,595 B2 | 5/2003 | Suzuki et al. | |
| 6,583,111 B1 | 6/2003 | DiMarchi | |
| 6,641,553 B1 | 11/2003 | Chee et al. | |
| 6,984,655 B1 | 1/2006 | Mori et al. | |
| 7,638,139 B2 | 12/2009 | Peyman | |
| 8,324,344 B2 | 12/2012 | Kisiel | |
| 8,808,268 B2 * | 8/2014 | Peyman ............. A61K 41/0028 604/20 |
| 2002/0174743 A1 | 11/2002 | Mukherjee et al. | |
| 2003/0014089 A1 | 1/2003 | Chow et al. | |
| 2003/0022374 A1 | 1/2003 | Greenbaum et al. | |
| 2004/0003839 A1 | 1/2004 | Curtain | |
| 2005/0004625 A1 | 1/2005 | Chow | |
| 2006/0173362 A1 | 8/2006 | Toms | |
| 2010/0185260 A1 | 7/2010 | Olson | |
| 2010/0211146 A1 | 8/2010 | Strowbridge et al. | |
| 2011/0270153 A1 | 11/2011 | Olson | |

OTHER PUBLICATIONS

Gao et al. In vivo molecular and cellular imaging with quantum dots. 2005 Curr. Opin. Biotechnol. 16: 63-72.*
Darsow et al. ETFAD/EADV eczema task force 2009 position paper on diagnosis and treatment of atopic dermatitis. 2010 J. Eur. Acad. Dermatol. Venereol. 24: 317-328.*
Hort et al. EFNS guidelines for the diagnosis and management of Alzheimer's disease. 2010 Eur. J. Neurol. 17: 1236-1248.*
Weissenstein et al. Detection of circulating tumor cells in blood of metastatic breast cancer patients using a combination of cytokeratin and EpCAM antibodies. 2012 BMC Cancer 12: 206, 8 pages.*
Aguilera et al. "Systemic in vivo distribution of activatable cell penetrating peptides is superior to cell penetrating peptides," Integr Biol (Camb), vol. 1, No. 5-6 (2009), pp. 371-381.
Akbarzadeh et al. Liposome: classification, preparation, and applications. Nanoscale Research Letters 8:102 (2013) 1-9.
Alavarez-Lorenzo et al., "Temperature-sensitive chitosan-poly(N-isopropylacrylamide) interpenetrated networks with enhanced loading capacity and controlled release properties" J. Controlled Release 102(3), (2005) 629-641.
Algar and Krull. Toward a Multiplexed Solid-Phase Nucleic Acid Hybridization Assay Using Quantum Dots as Donors in Fluorescence Resonance Energy Transfer. Anal Chem. 81 (2009) 4113-4120.
Andor Technology, "Transport Across the Nuclear Membrane Using Quantum Dots," Aug. 23, 2011, available at andor.com/company/news/?docID=1224.
Anscombe "Quantum Dots: Small Structures Poised to Break Big" Photonics Spectra, Jul. 2005, pp. 94-96.
Armand et al. The Emerging Role of Targeted Therapy for Hematologic Malignancies: Update on Bortezomib and Tipifarnib. The Oncologist 12 (2007) 281-290.

(Continued)

*Primary Examiner* — Michael G. Hartley
*Assistant Examiner* — Jennifer Lamberski
(74) *Attorney, Agent, or Firm* — The Law Office of Patrick F. O'Reilly III, LLC

(57) ABSTRACT

A method for early stage pathology detection, location, imaging, evaluation, and treatment of cells and/or extracellular vesicles in the circulation.

22 Claims, No Drawings

(56) References Cited

OTHER PUBLICATIONS

Audero et al. Sporadic Autonomic Dysregulation and Death Associated with Excessive Serotonin Autoinhibition. Science, vol. 321 (2008), pp. 130-133.
Aylott "Optical nanosensors-an enabling technology for intracellular measurements" Analyst, vol. 128 (2003), pp. 309-312.
Bakalova et al., "Quantum Dot-Conjugated Hybridization Probes for Preliminary Screening of siRNA Sequences" J. Am. Chem. Soc., (2005), 127 (32), pp. 11328-11335.
Baker and Baker. Luminescent Carbon Nanodots: Emergent Nanolights. Angew. Chem. Int. Ed. 49 (2010) 6726-6744.
Balasubramaniam et al., "Poly(N-isopropylacrylamide)-Coated Superaramagnetic Iron Oxide Nanoparticles: Relaxometric and Fluorescence Behavior Correlate to Temperature-Dependent Aggregation" Chem. Mater., 2011, 23, 3348-3356.
Beaupre et al. R115777 induces Ras-independent apoptosis of myeloma cells via multiple intrinsic pathways. Mol Cancer Ther 3 (2004) 179-186.
Benyettou et al., "Magnetoliposome for alendronate delivery" J. Mater. Chem., 21 (2011) 4813-4820.
Biju et al., Delivering quantum dots to cells: bioconjugated quantum dots for targeted and nonspecific extracellular and intracellular imaging. Chem. Soc. Rev. 39 (2010) 3031-3056.
Booth et al. Exosomes and HIV Gag bud from endosome-like domains of the T cell plasma membrane. *The Journal of Cell Biology*, vol. 172, No. 6, Mar. 13, 2006, 923-935.
Boyden, "Optogenetics: Using Light to Control the Brain," The Dana Foundation, Nov. 30, 2011, available at dana.org/news/cerebrum/detail.aspx?id=34614.
Buchen, "Illuminating the Brain," Nature, vol. 465, May 6, 2010, pp. 26-28.
Buck et al. "Optochemical nanosensor PEBBLEs: photonic explorers for bioanalysis with biologically localized embedding" Current Opinion in Chemical Biology, vol. 8 (2004), pp. 540-546.
Budgin et al. "Functionalization of Magnetic Nanoparticles with Amphiphilic Block Copolymers: Self-Assembled Thermoresponsive Submicrometer Particles" Langmuir 28 (2012) 4142-4151.
Cullum et al. "The development of optical nanosensors for biological measurements" Tibtech, vol. 18 (2000), pp. 388-393.
De Crespigny et al. Magnetic Resonance Imaging Assessment of Cerebral Hemodynamics During Spreading Depression in Rats. Journal of Cerebral Blood Flow and Metabolism, vol. 18 (1998), pp. 1008-1017.
Deisseroth "Optogenetics" Nature Methods, Published online Dec. 20, 2010, available at stanford.edu/group/dlab/papers/deisserothnature2010.pdf.
Deisseroth, "Optogenetics: Controlling the Brain with Light [Extended Version]," Scientific American, Published online Oct. 20, 2010, available at scientificamerican.com/article.cfm?id=optogenetics-controlling.
Delehanty et al., Self-Assembled Quantum Dot-Peptide Bioconjugates for Selective Intracellular Delivery. Bioconjug Chem 17 (2006) 920-927.
Derfus et al. "Targeted Quantum Dot Conjugates for siRNA Delivery" Bioconjugate Chem., vol. 18, No. 5 (2007) pp. 1391-1396.
Ding et al. Farnesyltransferase inhibitor tipifarnib inhibits Rheb prenylation and stabilizes Bax in acute myelogenous leukemia cells. Haematologica 99 (2014) 60-69.
Dixit et al. "Quantum Dot Encapsulation in Viral Capsids" Nano Letters, vol. 6, No. 9 (2006), pp. 1993-1999.
Duan and Nle. Cell-penetrating quantum dots based on multivalent and endosome-disrupting surface coatings. J. Am. Chem. Soc. 129 (2007) 3333-3338.
Dubertret et al., "In vivo Imaging of Quantum Dots Encapsulated in Phospholipid Micelles," Science, vol. 298, No. 5599 (2002), pp. 1759-1762.

Ebenstein et al. "Combining atomic force and fluorescence microscopy for analysis of quantum-dot labeled protein—DNA complexes" J. Molecular Recognition, vol. 22, issue 5 (2009), pp. 397-402.
Erogbogbo et al. Plasmonic gold and luminescent silicon nanoplatforms for multimode imaging of cancer cells. Integr. Biol. 5 (2013) 144-150.
Farokhzad et al., "Impact of Nanotechnology on Drug Delivery" ACS Nano 3(1) 2009, 16-20.
Fehr et al. "Development and use of fluorescent nanosensors for metabolite imaging in living cells" Biochemical Society Transactions, vol. 23, part 1 (2005), pp. 287-290.
Fei et al. "Glucose nanosensors based on redox polymer/glucose oxidase modified carbon fiber nanoelectrodes" Talanta, vol. 65 (2005), pp. 918-924.
Ferreira et al. "Downstream processing of plasmid DNA for gene therapy and DNA vaccine applications," Tibtech, vol. 18 (2000), pp. 380-387.
Filipa et al., "Polyelectrolyte-Coated Unilamellar Nanometer-Sized Magnetic Liposomes" Langmuir 2009, 25(12), 6793-6799.
Gao et al. In vivo cancer targeting and imaging with semiconductor quantum dots. Nature Biotechnology 22 (2004) 969-976.
Gill et al. " Fluorescence Resonance Energy Transfer in CdSe/ZnS—DNA Conjugates: Probing Hybridization and DNA Cleavage" J. Phys. Chem. B, vol. 109, (2005), pp. 23715-23719.
Greenbaum et al. "Application of Photosynthesis to Artificial Sight" paper presented at the Nanoscale Science and Technology in Medicine Symposium, 23rd International Conference of the IEEE Engineering in Medicine and Biology Society, Oct. 25-28, 2001, Istanbul, Turkey, vol. 4, pp. 4089-4091.
Gussin et al. Binding of Muscimol-Conjugated Quantum Dots to $Gaba_c$ Receptors. J. Am Chem. Soc. 128 (2006) 15701-15713.
Haes et al. "A unified view of propagating and localized surface plasmon resonance biosensors" Anal. Bioanal. Chem, vol. 379 (2004), pp. 920-930.
Haferlach. Molecular Genetic Pathways as Therapeutic Targets in Acute Myeloid Leukemia. Hematology (2008) 400-411.
Hauser and Zhang, "Peptides as biological semiconductors," Nature, vol. 468 (2010), p. 516.
He et al. Highly Luminescent Water-Dispersible Silicon Nanowires for Long Term Immunofluorescent Cellular Imaging. Angew. Chem. Int. Ed. 50 (2011) 3080-3083.
Heath et al., Varying Polymer Architecture to Deliver Drugs AAPS J. 9 (2007) Nanotechnology and Drug Delivery, article 26 (aapsj.org) E235-E240.
Heiss et al. Image-guided convection-enhanced delivery of muscimol to the primate brain. J Neurosurg. 112 (2010) 790-795.
Ho et al., Combining QD-FRET and Microfluidics to Monitor DNA Nanocomplex Self-Assembly in Real-Time. J. Vis Exp. 30 (2009) 1432, 3 pages.
Hoare et al. "A Magnetically-Triggered Composite Membrane for On-Demand Drug Delivery," Nano Lett. 9 (2009) 3651-3657.
Hofmann-Amtenbrink et al. Superparamagnetic nanoparticles for biomedical applications. Nanostructured Materials for Biomedical Applications, (ed. M.C. Tan.) 2009, chap. 5, 119-149.
Hohne et al. Acetazolamide prevents hypoxic pulmonary vasoconstriction in conscious dogs. J. Appl. Physiol. vol. 97 (2004), pp. 515-521.
Hong et al. Phase I Trial of a Combination of the Multikinase Inhibitor Sorafenib and the Farnesyltransferase Inhibitor Tipifarnib in Advanced Malignancies. Clin Cancer Res 15 (2009), 7061-7068.
Huang et al. Intermolecular and Intramolecular Quencher Based Quantum Dot Nanoprobes for Multiplexed Detection of Endonuclease Activity and Inhibition, Anal. Chem. 83 (2011) 8913-8918.
IBM Press Release, Made in IBM Labs: IBM Scientists Demonstrate World's Fastest Graphene Transistor, Feb. 5, 2010, 1 page.
Jarnagin et al. Treatment of cholangiocarcinoma with oncolytic herpes simplex virus combined with external beam radiation therapy. Cancer Gene Therapy 13 (2006) 326-334.
Jin et al. Preparation and Characterization of Highly Fluorescent, Glutathione-coated Infrared Quantum Dots for in Vivo Fluorescence Imaging. Int. J. Mol. Sci. 9 (2008) 2044-2061.

(56) References Cited

OTHER PUBLICATIONS

Joeres et al. Quantitative Comparison of Optical Coherence Tomography after Pegaptanib or Bevacizumab in Neovascular Age—Related Macular Degeneration. Ophthalmology 115 (2008) 347-354.
Joo et al. "Enhanced Real-Time Monitoring of Adeno-Associated Virus Trafficking by Virus—Quantum Dot Conjugates" ACS Nano, vol. 5, No. 5 (2011), pp. 3523-3535.
Karp et al. Multi-institutional phase 2 clinical and pharmacogenomic trial of tipifarnib plus etoposide for elderly adults with newly diagnosed acute myelogenous leukemia. Blood 119 (2012) 55-63.
Kelley. "What Clinicians Need to Know About Molecular Markers in Solid Tumors" Aug. 6, 2010, available at medscape.org/viewarticle/725989.
Kim and Taton. Multicomponent nanoparticles via self-assembly with cross-linked block copolymer surfactants. Langmuir, 23 (2007) 2198-2202.
Kleiner et al. Farnesyl and geranylgeranyl transferase inhibitors:an anti-inflammatory effect. Comment to "Inhibition of protein geranylgeranylation and farnesylation protects against graft-versus-host disease via effects on CD4 effector T cells" haematological 98 (2013) e44-e45.
Kurzrock et al. Phase I Study of Alternate-Week Administration of Tipifarnib in Patients with Myelodysplastic Syndrome. Clin Cancer Res 14 (2008) 509-514.
Kurzweil AI, Engineers envision 2-dimensional grapheme metamaterials and 1-atom-thick optical devices. Jun. 10, 2011, 1 page; internet address: kurzweilai.net/engineers-envision-2-dimensional-graphene-metamaterials-and-1-atom-thick-optical-devices.
Lee et al. The retinoblastoma susceptibility gene encodes a nuclear phosphoprotein associated with DNA binding activity. Nature, 329(1987) 642-645.
Leite, et al. PE and PS Lipids Synergistically Enhance Membrane Poration by a Peptide with Anticancer Properties. Biophysical Journal 109 (2015) 936-947.
Lim et al. "Specific Nucleic Acid Detection Using Photophysical Properties of Quantum Dot Probes" Anal. Chem., vol. 82, No. 3 (2010), 886-891.
Liu et al. Bioconjugated Pluroinc Triblock-Copolymer Micelle-Encapsulated Quantum Dots for Targeted Imaging of Cancer: In Vitro and In Vivo Studies. Theranostics 2 (2012) 705-713.
Liu et al., Cell-Penetrating Peptide-Functionalized Quantum Dots for Intracellular Delivery. J. Nanosci. Nanotechnol. 10 (2010) 7897-7905.
Liu et al., Cellular Internalization of Quantum Dots Noncovalently Conjugated with Arginine-Rich Cell-Penetrating Peptides. J. Nanosci. Nanotechnol. 10 (2010) 6534-6543.
Liu et al., Endocytic Trafficking of Nanoparticles Delivered by Cell-penetrating Peptides Comprised of Nona-arginine and a Penetration Accelerating Sequence, PLOS One 8 (2013) e67100, 12 pages.
Liu et al., Intracellular Delivery of Nanoparticles and DNAs by IR9 Cell-penetrating Peptides, PLOS One 8 (2013) e64205 (13 pages).
Lugo et al. Remote switching of cellular activity and cell signaling using light in conjunction with quantum dots. Biomedical Optics Express 3. (2012) 447-454.
Lv et al., Surface modification of quantum dots and magnetic nanoparticles with PEG-conjugated chitosan derivatives for biological applications. Chemical Papers 67 (2013) 1404-1413.
Mali et al. "Intravitreous Injection of a Membrane Depolarization Agent Causes Retinal Degeneration via Matrix Metalloproteinase-9" Investigative Ophthalmology and Visual Science, vol. 46, No. 6 (2005), pp. 2125-2132.
Michalet et al., "Quantum Dots for Live Cells, in Vivo Imaging, and Diagnostics," Science, 307, No. 5709 (2005), pp. 538-544.
Min et al. Lentivirus—Mediated sFlt-I Gene Fragment Transfer Suppresses Retinal Neovascularization. Current Eye Research 34 (2009) 401-410.
Momet et al., "Magnetic nanoparticle design for medical diagnosis and therapy," J. Mater. Chem., 14 (2004) 2161-2175.
Mossman "Quantum dots track who gets into cell nucleus" Physorg.com, Sep. 2, 2010, available at .physorg.com/news202628740.html.
Mulder et al. Quantum dots for multimodal molecular imaging of angiogenesis. Angiogenesis 13 (2010) 131-134.
Nguyen et al. "Surgery with molecular fluorescence imaging using activatable cell-penetrating peptides decreases residual cancer and improves survival," Proc. Nat. Acad. Sci., 107 (2010) 4317-4322.
Olson et al. "Activatable cell penetrating peptides linked to nanoparticles as dual probes for in vivo fluorescence and MR imaging of proteases," Proc. Nat. Acad. Sci. 107 (2010) 4311-4316.
Olson et al. "In vivo characterization of activatable cell penetrating peptides for targeting protease activity in cancer," Integr Biol, 1 (2009) pp. 382-393.
Pan et al. Silica Cross-linked Micelles Loading with Silicon Nanoparticles: Preparation and Characterization. ACS Appl. Mater. Interfaces 5 (2013) 7042-7049.
Pappas et al. Nanoscale Engineering of a Cellular Interface with Semiconductor Nanoparticle Films for Photoelectric Stimulation of Neurons. Nano Letters 7 (2007) 513-519.
Peyman et al. A High-Resolution 3D Ultrasonic System for Rapid Evaluation of the Anterior and Posterior Segment. Ophthalmic Surgery, Lasers & Imaging 43 2012) 143-151.
Pothayee et al., "Magnetic Block Ionomer Complexes for Potential Dual Imaging and Therapeutic Agents" Chem. Mater. 2012, 24 2056-2063.
Rajan and Raj. Potential Drug Delivery Applications of Chitosan Based Nanomaterials. I.Re.CH.E. 5 (2013) 145-155.
Rio-Portilla et al. REM Sleep Post-Eye Movement Activation. International Journal of Bioelectromagnetism, vol. 10, No. 4 (2008), pp. 192-208.
Rosenthal et al. Biocompatible Quantum Dots for Biological Applications. Chem Biol. 18 (2011) 10-24.
Sander et al. CRISPR-Cas systems for editing, regulating and targeting genomes. Nature Biotechnology 32:4 (2014) 347-355.
Sexton et al. "A Protective Vaccine Delivery System for In Vivo T Cell Stimulation Using Nanoengineered Polymer Hydrogel Capsules," ACS Nano, vol. 3, No. 11 (2009), pp. 3391-3400.
Singerman. Combination therapy using the small interfering RNA bevasiranib. Retina 2009, Abstract Only.
Smith et al., Bioconjugated Quantum Dots for In Vivo Molecular and Cellular Imaging. Adv. Drug Deliv. Rev. 60 (2008) 1226-1240.
Song et al., Tumor Cell Targeting Using Folate-Conjugated Fluorescent Quantum Dots and Receptor-Mediated Endocytosis. Clinical Chemistry 55 (2009) 955-963.
Suzuki et al. Quantum Dot FRET Biosensors that Respond to pH, to Proteolytic or Nucleolytic Cleavage, to DNA Synthesis, or to a Multiplexing Combination. J. Am. Chem. Soc. 130 (2008) 5720-5725.
Tai et al. "Thermosensitive liposomes entrapping iron oxide nanoparticles for controllable drug release" Nanotechnology 20 (2009) 135101 (9 pages).
Templeton. Tiny Q-dots may enable more precise brain surgery. Pittsburgh Post-Gazette, Apr. 10, 2007, 4 pages.
Tomczak et al. Designer polymer-quantum dot architectures. Progress in Polymer Science, 34 (2009) 393-430.
van Rooy et al. Comparison of five different targeting ligands to enhance accumulation of liposomes into the brain. Journal of Controlled Release 150 (2011) 30-36.
Wang et al. Nucleic Acid Conjugated Nanomaterials for Enhanced Molecular Recognition. ACS Nano 3 (2009) 2451-2460.
Wen et al. Theranostic liposomes loaded with quantum dots and apomorphine for brain targeting and bioimaging. International Journal of Nanomedicine 7 (2012) 1599-1611.
Xu et al. "Controlled Release and Assembly of Drug Nanoparticles via pH-Responsive Polymeric Micelles: A Theoretical Study" J. Phys. Chem. B, 2012,116 (20), 6003-6009.
Xu et al., Nona-Arginine Facilitates Delivery of Quantum Dots into Cells via Multiple Pathways. J. Biomedicine and Biotechnology 2010, Article ID 948543, 11 pages.
Yanamandra et al. Tipifarnib and Bortezomib Are Synergistic and Overcome Cell Adhesion-Mediated Drug Resistance in Multiple Myeloma and Acute Myeloid Leukemia. Clin Cancer Res 12 (2006) 591-599.

(56) References Cited

OTHER PUBLICATIONS

Yezhelyev et al., Proton-Sponge-Coated Quantum Dots for siRNA Delivery and Intracellular Imaging. J Am. Chem. Soc. 130 (2008) 9006-9012.

Yizhar et al., "Optogenetics in Neural Systems," Neuron, vol. 71 (2011), 9-34.

You et al. Incorporation of quantum dots on virus in polycationic solution. Int. J. Nanomedicine 1 (2006) 59-64.

Zhang et al., "Optogenetic interrogation of neural circuits: technology for probing mammalian brain structures," Nature Protocols, vol. 5, No. 3 (2010), pp. 439-456.

Zhong et al. Modular design of an ultrahigh-intensity nanoparticle probe for cancer cell imaging and rapid visual detection of nucleic acids. Chem Commun., 48 (2012) 6277-6279.

Narayanan et al., Mimicking cellular transport mechanism in stem cells through endosomal escape of new peptide-coated quantum dots. Scientific Reports 3, article No. 2184, 6 pages, Jul. 15, 2013.

\* cited by examiner

EARLY DISEASE DETECTION AND THERAPY

This application claims priority to U.S. Ser. No. 62/303,219 filed Mar. 3, 2016 and expressly incorporated by reference herein in its entirety.

A method for early detection of pathologies such as cancer or metabolic disorders by detecting and evaluating metabolic markers and early stage cells in the retinal circulation. The inventive method renders blood cellular compositions and components indirectly visible and quantifiable by various imaging modalities. This provides means of early disease detection, diagnosis, and treatment.

The retinal circulation stems from the central retinal artery, which is the first branch of the internal carotid artery. The central retinal artery enters the optic nerve 4 mm-5 mm behind the eyeball, and divides into four branches at the optic nerve head, further branching to vascularize the four retinal quadrants.

Retinal tissue is transparent. The retina thus permits visualization and provides a window into the invisible internal circulation. Taking advantage of retinal transparency thus provides an opportunity for unhindered visualization and examination of, among other components, the composition of blood. As one example, cell types and the metabolic state of cells, among other features, can be determined. More specifically, photoacoustic technology permits examination, at the molecular level, of cellular analyte type and concentration, e.g., oxygen, carbon dioxide, sugar, etc. As another example, free circulating tumor cells (CTC) and extracellular vesicles (ECV) such as exosomes can be visualized, assessed, quantified, etc.

Malignant tumors have the capability to metastasize at an early stage, even before the tumor has grown to 3 mm-4 mm in diameter, the point at which they are visible by standard imaging techniques such as computed tomography, magnetic resonance imaging, etc. Such small tumors are not space occupying and often do not produce clinical symptoms in patients, even patients having a genetic predisposition to the pathology are often not aware of its development. It is also difficult to diagnose recurrences of a cancer if a tumor has not yet grown to a size that is radiologically visible. In addition, there is often there is no visible indication of tumor cell activity within a tumor mass after, e.g., radiation therapy or at the margin of a resected lesion for a long time. Tumor growth is currently but erroneously considered as the only sign of tumor activity, but there are many examples where metastatic lesions suddenly grow after years while the patient is considered in remission.

The method permits distinction and differentiation between a malignant lesion and a benign lesion. As only one example, the method can differentiate a malignant but early melanoma of the choroid, the vascular layer of the eye, from a benign choroidal nevus.

In use, a blood sample is obtained from a patient suspected to have a pathology. The blood sample is evaluated for signs of tumor activity by analyzing the sample for the presence of various molecular tumor biomarkers, proteins, microDNA, microRNA, enzymes, nucleosomes, extracellular vesicles, free floating tumor cells, etc. In one embodiment, the blood sample is analyzed for the presence of cancer, and/or various disease biomarkers, including cancer biomarkers, as disclosed in co-pending U.S. Ser. No. 14/976,321 filed Dec. 21, 2015 which is expressly incorporated by reference herein in its entirety.

In one embodiment, an antibody to either a specific tumor or a non-specific tumor is generated in vitro or ex vivo using standard techniques known the art. The antibody may be any type, e.g., polyclonal, monoclonal, humanized, aptamers, etc. The generated antibodies are then used to coat nanoparticles including but not limited to quantum dots (QD) nanoparticles, forming functionalized nanoparticles. The antibody-coated functionalized nanoparticles are injected into the patient's circulation, where they target their corresponding tumor cell membrane receptor antigen. Alternatively, the antibody-coated functionalized nanoparticles are injected in the circulation where they target and bind to not only to the sessile site of the tumor, but also target and bind to free circulating tumor cells and their free floating extracellular vesicles (ECV) or exosomes. The user, after waiting for about 1 min to about 8 min for targeting and binding to occur, then uses photoacoustic technology to image the tumor site and/or circulating cells, as previously described in U.S. Ser. No. 14/976,321.

In one embodiment the nanoparticles range in size from about 1 nm to 500 nm, preferably between 1 nm-10 nm. In one embodiment, the nanoparticles range in size from about 1 nm-8 nm, 8 mm-20 nm, 30 nm-50 nm, or 50 nm-900 nm in diameter.

The exact composition of the functionalized nanoparticle, i.e., both the type of nanoparticle(s), and the type of antibody coating the nanoparticles, can be specific for one or many biomarkers for different tumors or tumor types or tumor sets. The nanoparticle can be coated with cell penetrating agents, e.g., cell-penetrating peptide (CPP), activated CPP (ACPP), etc., eliminating a viral carrier that induces an immune response and cannot be administered repeatedly. That is, the inventive method desirably is performed in the absence of a viral carrier.

In one embodiment, the nanoparticles are quantum dots, either alone or in combination with other nanoparticles. As known in the art, quantum dots may be organic, inorganic, synthetic, magnetic, paramagnetic, non-magnetic, nano/microbubble, piezoelectric, etc.; the nanoparticle structure(s) can include a shell, cage, wire, tube, or other configuration, and the shape may be spherical, cylindroid, tube, multifaceted, etc.; nanoparticle compositions may be gold, silica, iron, iron oxide, zinc, zinc oxide or their composites, cadmium sulfate, quartz and other piezoelectric nanoparticles, lanthanide or other upconverting nanoparticles, i.e., quantum dot nanoparticles that are excited with two photons of a near infrared wavelength or infrared light and emit one photon of higher energy wavelength of blue to red visible wavelengths, copper, nickel, carbon, or graphene located in the core and/or the nanoparticle surface. The composition of the nanoparticle, e.g., gold, iron, iron oxide, etc. may be functionalized with antibody to specific cell membranes and injected into the circulation to adhere to a tumor, e.g. in the eye, skin, mucosa, etc. The nanoparticles may be coated with a radioactive alpha, beta, or gamma emitter molecule to add the effect of radiation therapy to other therapies such as photodynamic therapy (PDT), thermotherapy, chemotherapy (drug release), etc. In one embodiment gold or iron nanoparticles are coated as previously described to seek the desired cells, then low x-ray radiation is applied to the lesion, e.g., neovascular tissue or a tumor such as melanoma, alone or in conjunction with PDT or thermotherapy. In one embodiment gold nanoparticles are coated as previously described and injected into the circulation to attach to the desired cells, then low dose thermal or x-ray radiation or femtosecond laser pulses to a continuous pulse laser are provided to produce free radicals. The free radicals damage walls of endothelial cells, causing a photodynamic effect with free radical and singlet oxygen formation and platelet aggregation and vascular occlusion. This embodiment may be combined with local drug delivery, such antiproliferative agents, anticancer agents, anti-VEGF agents such as cisplatin that enhances formation of reactive oxygen species. This embodiment may be combined with very low dose systemic administration of medication.

In one embodiment, the composition of the circulating elements is differentiated by size, as rendered visible in the retinal circulation and recorded, as further disclosed, by the adherent nanoparticles. As an example, ECV range in size from 100 nm-500 nm, and tumor cells to which nanoparticles adhere typically range in size from 5 microns-20 microns.

In one embodiment, nanoparticles with a specific anti-tumor antibody, upon stimulation, emit light of a specific wavelength that is detectable by fundus photography, angiography, optical coherence tomography (OCT), and/or OCT angiography (OCTA) as subsequently described. This wavelength of emitted light provides information on the origin of the specific sessile or particulate circulating in the blood or other fluids to which the plurality of nanoparticles containing specific tumor antibodies are attached. Each quantum dot nanoparticle, depending on its size and composition after light stimulation, produces a different wavelength of light, which is specific to its size and composition. If the nanoparticle size or composition and the specific antibody coating (e.g. breast cancer) is known prior to administration in the circulation, the quantum dots seek specific membrane antigens to which to adhere. When stimulated by a light beam, they emit a wavelength of light with a specific wavelength (color) that indicates which nanoparticle/antibody is attached to which cells or cell types that have the specific cell membrane receptor, thereby revealing the identity of that circulating cell, exosome, etc. In one embodiment, after stimulation of the quantum dot nanoparticles with various wavelengths of external light, a fluorescein angiography fundus camera records the light emitted by nanoparticles from inside the retinal vessels. These cameras are modified to have specific barrier filters that separate the incoming stimulating light from the quantum dot emitted exiting light. In this embodiment, the different wavelength of light (colors) emitted by the stimulated quantum dot nanoparticles in the retinal vessels function as an optical spectroscopic system that are recorded, indicating the presence of a specific circulating tumor cell and/or ECV in the circulation. This provides a non-invasive method of imaging, and also provides a method of early cancer detection and differentiation based on wavelength differentiation, i.e., optical spectroscopy), which may then be treated by a specific therapy.

In one embodiment, after the nanoparticles have been stimulated with light of different wavelengths, the nanoparticles emit a fluorescent wavelength that is diagnostic for an actively dividing tumor cell. This is based on the principle that the stimulating wavelength of light is different from emitted light from the stimulated quantum dots. This wavelength differentiates the nanoparticles by size; a smaller size produces a blue wavelength, whereas a larger size produces a longer wavelength such as red. Because the nanoparticles are functionalized with one or more specific antibody or antibodies, it thus also differentiates the nanoparticles bound to a cell containing the specific cell membrane antigen to which the nanoparticles are conjugated. Thus, once the nanoparticles are attached to these circulating cells or ECV, the nanoparticles act as a diagnostic for the presence of the tumor from which the cells or the ECV originate, and they can be tracked and counted by the camera's photometer. In one embodiment, performing the method using a plurality of nanoparticles with different sizes and/or compositions and/or different antibody coatings provides a myriad of diagnostic capabilities for diagnosing numerous active tumors, their cellular origin, and their ECVs.

In one embodiment, the retina is radiated, e.g., with focused electromagnetic radiation, or low dose microwave radiation, or radiofrequency radiation, to increase the temperature of the circulating nanoparticles in the retinal and choroidal circulation. Using photoacoustic imaging technology, a photoacoustic spectroscopy of the antibody-coated nanoparticles, attached to the free floating cells or exosomes, is obtained. The free floating cells or exosomes are thus imaged, and the specific lesions are diagnosed in the eye or other body sites, and/or quantified.

In one embodiment, a light beam from a laser is focused continuously on a specific retinal vessel through a contact lens positioned on the cornea of the patient, after application of a topical anesthesia. The ultrasound receiver of the photoacoustic technology system is attached to any of the side of the eye, lid of the eye, or the forehead proximal to the eye. The operator observes the laser beam focused on a retinal vessel while the retina is under observation through a slit lamp microscope. The photoacoustic system is connected to the laser delivery system via a computer. The operator adjusts the photoacoustic system so that it controls, via the computer, the thermal energy delivered by the laser to achieve a photoacoustic or thermoacoustic response, i.e., sound wave, representing a temperature of about 38° C. to 45° C. from the heated nanoparticles. Because the nanoparticles that are circulating in the retinal vessel absorb the laser energy to a greater degree compared to their surrounding milieu or environment, the nanoparticles' thermal expansion produces a photoacoustic sound wave. This photoacoustic sound wave is recorded by the transducer of a photoacoustic unit, indicating the presence of circulating nanoparticle-cell complexes and/or nanoparticle-ECV complexes in the retinal vessel. The larger circulating cells will have more nanoparticles attached to their cell membrane than the ten-times smaller extracellular vesicles, and will appear larger by photoacoustic imaging. Thus, these two structures are differentiated based on their size. The origin of these cells or ECV can be differentiated by the antibody coated used prior to administration of the nanoparticles functionalized to a specific tumor receptor. Using different laser wavelengths as previously described, with the laser focused on the retinal vessel the quantum dot nanoparticles that absorb a specific wavelength and emit at a different wavelength depending on their size, etc. the fundus camera that has a standard fluorescence angiography system is modified so that a photometer or a detector absorbs that presence of different wavelength pulses emitted from the quantum dots as they pass through the laser spot focused on a retinal vessel. This photometer, as other detectors known in the art of optical spectroscopy, converts radiant power into an electrical signal that can be processed, recorded, and displayed. This system thus provides information on the number of light pulses generated, with the color or wavelength indicating the number of cells or ECV recorded at a given time. The emitted color is indicative of the quantum dot that produced it, which in turn indicates its size and the identity of the antibody that coated that size of quantum dot. Because the quantum dots are antibody coated to specific cell membrane receptors, one can determine the number of those circulating cells or tumor cells, or their ECV, that are circulating at a given time.

As previously analyzed, the amplitude of this acoustic response is in direct relationship with the size and the composition of these nanoparticles. The smaller nanoparticles absorb energy faster than the larger nanoparticles and show a higher temperature than the larger nanoparticles. Thus, the smaller nanoparticles expand faster, and produce a photoacoustic sound with higher amplitude and frequency, than larger nanoparticles. Because the nanoparticles are coated with one or more specific antibody or antibodies against the specific cell of interest, e.g. a tumor cell, the origin of the cell type or ECV can be recognized by the photoacoustic unit's processor that differentiates the amplitude and frequency of these sound waves, as in photoacoustic spectroscopy techniques, and separates each group of sounds from each other group of sounds, indicating the number and size of all specifically coated nanoparticles that have passed through the laser spot light.

As an example, functionalized ferric oxide nanoparticles of a certain size can be coated with a specific antibody to a specific tumor, indicating the presence of that specific tumor or other tumors in the body. The groups of nanoparticles, depending upon size, are coated with a different antibody, e.g., those 1 nm-up to 15 nm in diameter are coated with one antibody, and those 15 nm-up to 30 nm in diameter are coated with a second antibody, and those 30 nm-up to 50 nm, 50 nm-up to 100 nm in diameter, 100 nm-up to 200 nm in diameter, 200 nm-up to 300 nm in diameter, 300 nm-up to 400 nm in diameter, 400 nm-up to 500 nm in diameter, up to about 900 nm, etc., are coated with different antibodies for different tumors.

Photoacoustic spectroscopy can quantify and differentiate which tumors have produced an ECV or circulating tumor cell. Results obtained by photoacoustic spectroscopy are compared and validated with results using optical spectroscopy of the cells using quantum dot nanoparticles that emit specific wavelengths of light upon stimulation. Using these results, one can search for the origin of the tumor using a hand-held photoacoustic unit, as described in detail in U.S. Ser. No. 14/976,321 filed Dec. 21, 2015 which is expressly incorporated by reference herein in its entirety.

The origin of these cells or the ECV can be differentiated by the antibody coating used prior to the administration of the functionalized nanoparticles to specific tumor cell receptors. Using different laser wavelength as described above, with the laser focused on the retinal vessel, the nanoparticle that absorbs the specific wavelength and emits another wavelength depending on its size etc., the fundus camera that has a standard fluorescence angiography system is modified so that a photometer absorbs that presence of different wavelength pulses emitted from the nanoparticles as they pass through the laser spot focused on a retinal vessel. This photometer recording acts like an ordinary spectroscope giving information on the number of light pulses generated with what color or wavelength indicating the number of cells or ECV recorded at a given time. The emitted color is indicative of what quantum dot produced it, which in turn indicates its size and which antibody that coated that size quantum dot. Because the quantum dots are antibody coated to specific cell membrane receptors, one can deduct how many of those circulating cells or tumor cells or their ECV circulate at a given time.

The thermal energy, e.g., electromagnetic radiation, focused microwave, radiofrequency, focused ultrasound wave, etc.) is applied and controlled by the photoacoustic system to any lesion to which the antibody-coated nanoparticles, by specific binding of the antibody to that antibody's specific antigen, directs the nanoparticles and to which the nanoparticles. The lesion may be, e.g., in the eye, skin, or other organs, etc. Using the photoacoustic system, the site of the lesion is heated to about 38° C. to 42° C. The photoacoustic system produces a thermal image of the nanoparticles that are attached, via specific antigen-antibody binding, to the specific tumor mass or infected lesion at any site to which the antibody is directed, in e.g., retina, choroid, skin, mucosa, brain, lung, heart, kidney, liver, temporal artery, etc. Through software within the photoacoustic system, a photoacoustic spectroscopy of each the plurality of nanoparticles that are coated with different tumor biomarkers, infective agent, etc. biomarker antibodies can be created, thereby revealing through their specific and known antibody coating the nature of the mass, suspected lesion area, infected tissue, etc. The result thus provides information on the nature or origin of the tumor cells, infective disease, etc.

In one embodiment, nanoparticles of 1 nm-8 nm can be conjugated with an antibody that, after injection into the circulation of eye cavity, target to specific cell receptors, e.g., receptors on leaky new vessels. The inventive method also provides two- or three-dimensional images by OCTA on the delicate small leaking sites of the blood occular barrier in the eye, or spinal cord, or brain, etc. due to the presence of the nanoparticle passing through the broken vessel or new vessel.

In one embodiment, antibodies coating, with cell penetrating agents such as CPP and/or ACPP, etc., inhibitory gene(s) alone or with the CRISPR complex, the nanoparticles are directed to microorganisms, e.g., bacteria, fungi, viruses, parasites, etc. These antibody-coated nanoparticles are injected systemically into the patient. Using the previously described photoacoustic technology, the nanoparticles bind to the corresponding antigens that are present on the free circulating organisms, or may be collected in the tissue of the retina, choroid, or elsewhere, e.g., in the skin. If bacterial antibody-coated nanoparticles are injected into the circulation and accumulate in the eye or skin, the nanoparticles can be heated by the previously described specific laser wavelength, producing a photoacoustic response that can be recorded by a photoacoustic system. This embodiment provides information about the origin of the infection, etc.

Nanoparticle assisted photography, angiography, OCT, OCT angiography (OCTA) is used for detection and therapy of a disease process, e.g., in the eye or elsewhere in the body.

OCT is based on low coherence tomography using light, and captures two-dimensional or three-dimensional images from the light scattered through and in the media through which it propagates. Using ophthalmology as an example because of transparent ocular media, OCT provides information about the anterior segment, the lens and the retina/anterior choroid. OCT has a potential application for imaging skin and its various disorders, and provides information on the thickness and borders of a skin lesion.

OCTA technology can image the retinal/choroidal vessels, vascular abnormalities, and any retinal/choroidal neovascularizations. In OCTA, consecutive B-scan images of the laser light provide a two- or three-dimensional cross-sectional image of tissues, such as the retina, to the limit of light penetration in the tissue. OCTA is based on the algorithm of split-spectrum amplitude decorrelation, which allows visualization of the inner and outer layer of the retinal vasculature and the choriocapillary of both inner and outer retinal vascular plexus and the choroidal capillary layer. OCTA contrasts the images obtained from the static tissue, e.g. retinal tissue, vs non-static tissue such as blood vessels.

OCTA decorrelates the signals, using associated software, and presents a three-dimensional image of the retinal vessels and choriocapilaries separately to a depth of about 10 micron below the Bruch's membrane.

Currently available OCTA systems provide an average axial resolution of about 15 micrometer and an average lateral resolution of about 5 microns. However, the resolution of the image is not sufficient to provide a signal from small molecules having a diameter of less than 500 nm-1 micron. Therefore at present, suspensions of, e.g. serum molecules, originating from leaky vessels in the choroid and retina, remain invisible with OCTA and appear as a dark space in OCT images. Using fluorescein angiography (FA), a much older technique, one sees passage of a fluorescein dye through the small discontinuity in the damaged wall of a leaky vessels. In a fluorescein angiography (FA) the dye becomes visible as a stained wall of a damaged vessel, or as a pool of dye collected in the interstitial spaces or cavities of diseased tissue, e.g. retina. Using fluorescein, the collected small molecules of the fluorescein dye remains invisible, or appear as dark spaces in the OCT and OCTA images and/or under the sensory retina. Therefore, OCT or OCTA do not compare well with standard fluorescein angiography in demonstrating leakage from abnormal or neovascular lesions or small defects in the retinal pigment epithelium or abnormal retinal vessels. The abnormal vessels or new vessels result from hypoxia causing adjacent tissues to produce vascular endothelial growth factor (VEGF), inducing neovascularization. Inflammatory diseases directly affect the blood retinal barrier, cause leakage of fluorescein outside the retinal vasculature. Pathologies such as age-related macular degeneration (ARMD), diabetic retinopathy, central serous retinopathy, stroke, etc. all induce damage to the retinal vasculature. In one embodiment, nanoparticles carry antibodies to VEGF to inhibit growth-inducing abnormal vessels or the vascular supply of a tumor.

FA has a number of shortcomings. One shortcoming is that the deeper retinal capillary plexus and radial peripapillary capillary network cannot be seen in FA due to scattering of the incidence light (blue) and reflected fluorescent light, and in the deeper retinal layers. Similarly, the invisibility of the peripapillary network in the FA renders FA not useful for evaluation of the progression of damage to the optic nerve head or retina in patients with glaucoma, etc. FA also has potential side effects such as nausea, vomiting, pruritus, urticaria, pyrexia, thrombophlebitis, and life threatening reactions such as anaphylaxis response, bronchospasm, cardiac arrest, and death. Local tissue necrosis can also occur with extravasation of the dye at the site of the injection. In addition the fluorescin angiogram cannot satisfactorily demonstrate the choroidal vessels well. As a result, the patient must undergo a second minimally invasive procedure, i.e., the so-called indocyanin green angiography, in which an infrared light is used to excite the dye, obtaining a fluorescent infrared wave length for imaging. Indocyanine green angiography has equal if not more side effects than fluorescein angiography, particularly life threatening side effects or death in patients with seafood or iodine allergies. Another problem is that both these dyes clear the circulation within a few minutes, and have no specificity to abnormal endothelial cells. They are also invisible with OCT technology because of their small molecular size. They also have no therapeutic effect on the disease process and are used only as an imaging tool.

The inventive method overcomes these deficiencies. It provides a method of angiography with new fluorescent quantum dot nanostructures. The quantum dots are themselves fluorescent; when stimulated by a specific wavelength of light, they emit a longer wavelength of light (fluorescent light). They act like fluorescein molecules, but are larger in size and their fluorescence does not bleach. In contrast, in fluorescein molecules, fluorescence bleaches and turns itself off beyond a certain time of light exposure. The quantum dots of 1 nm-8 nm can pass through the blood brain barrier at a site of minor discontinuity. As previously described, the cause of the discontinuity may an inflammatory process, abnormal vessels caused by hypoxia, vascular occlusion such as in diabetes or stroke, a neoplastic lesion, an infection, trauma, tumor, etc.

In one embodiment, quantum dot nanoparticles fluoresce, upon exposure to a specific wavelength of laser or diode light, at a specific wavelength with lower energy. Fluorescence or emitted light from the quantum dot nanoparticles passes, without being scattered by the transparent retinal tissue, through an appropriate barrier filter and can be captured by photograph or video camera.

In one embodiment, the light source that excites the nanoparticles, such as an infrared (IR) source, can simultaneously produce an OCT or an OCTA and which can be recorded separately by an OCT unit and software to produce OCT or OCTA images. The light that is generated from the quantum dot nanoparticles can also be separated from that of the OCT unit via an appropriate barrier filter diverted to be imaged by an angiographic camera separately, creating a combined OCT, OCTA, and fluorescent angiogram system. In one embodiment, infrared excitation light and lanthanide group nanoparticles are used because of the advantage of not being seen by the patient's photoreceptors, thus it does not blind the patient as does visible light. In addition, the same light can simultaneously produce the OCT and OCTA images. This unit requires only a simple infrared prism to divert the returning infrared light to the OCT unit, while permitting the emitted visible light coming through from the lanthanide nanoparticles to be picked up by the system's camera.

In one embodiment, the system provides an IR wavelength excitation and near-IR emission for use with nanoparticles of 1 nm up to 150 nm or even larger than 150 nm. The following elements or composites upconvert the light by absorbing two photons of a low energy light beam and upconvert it to one photon of higher energy beam, e.g., infrared to yellow or blue wavelengths, etc.: lanthanide nanoparticles family erbium, thulium, holium Ln, Ti, Ni, Mo, Re, Os, cerium, lanthnum, lutetium, yttrium, scandium, gadolinium fluoride, and lanthnum fluoride, or as a lanthanide rich composite as known in the art having one lanthanide ion from the group of Ce, Nd, ER, etc. in combination with an anion from a halide, phosphate, vanadate etc., or $LaAL0ri3/SrTiO3$, thulium-doped silica, gadelonium or neodynium complexes such as Nd—Fe—B, or semiconductors CdSe, PbSe, PbS. These nanoparticles upconvert the excitation light, converting two IR photons to a single visible light that can be photographed with a standard fundus camera, or video-angiography can be performed without producing the previously described side effects of fluoresceine or indocyanin green angiography.

In one embodiment, these nanoparticles are coated. The coating may be polymers such as (poly)ethylene glycol (PEG), chitosan, cell penetrating agents such as CPP, ACPP, etc., one part of the binding pair biotin/streptavadin, etc., as well as containing specific or non-specific antibodies to the desired cells. The antibodies seek abnormal vessels, e.g., found in age related macular degeneration or a tumor, and adhere to the vessel walls for subsequent treatment, under an operator's control and observation. The nanoparticles in any of these embodiments are injected in a biocompatible formulation for the various described indications. In one embodiment, coated nanoparticles are functionalized by conjugation with various cytokine antibodies. These cytokine antibodies, when injected into the circulation, attach to cytokine producing cells, e.g., anti-VEGF coated nanoparticles will localized in an area of a retina that is ischemic and thus that produces VEGF, IL-1, etc. The nanoparticles may be conjugated with cell penetrating peptides such as CPP or ACPP, etc. and an inhibitory gene/CRISRP cas9, to inhibit production of VEGF, other genes, siRNA, etc. or conjugated with IL inhibitory medication. Many diseases such as cancer produce an inflammatory environment, and diseases such as Alzheimer's disease or traumatic brain injury produce inflammatory insults. The inventive technology not only demonstrates and images the site of inflammation, but also potentially treats the inflammation with appropriate medication administered with the quantum dot nanoparticles. The system can also be used for an early stage disease process that can be treated, and the results of the treatment can be quantified.

This methodology can demonstrate the presence of the inflammatory biomarkers in some areas, indicating a part of a tissue affected by a pathology such as an infarct, or a disease state such as a neurodegenerative disease, e.g., Alzheimer's disease, infection, an autoimmune response, a genetic disorder, a tumor, etc. This area can be imaged photographically or using X-rays, MRI, CT, PET, etc., or by antibody coated nanoparticle assisted photoacoustic imaging or localized thermotherapy using electromagnetic radiation, RF, microwaves, focused ultrasound, alternating magnetic field, etc., and/or simultaneous drug release from the nanoparticles. In one embodiment, the nanoparticles, e.g., a lanthanide etc., is coated with a thermosensitive polymer such as chitosan and conjugated with an anti-VEGF cell specific antibody that attaches to vascular endothelial cells producing VEGF receptors in the retina or choroidal abnormal vessels or elsewhere in tumor vasculature. One can specifically make these abnormal vessels visible, image them, and treat them with various means such as a laser in the same session or by another source of energy such as microwave, radiofrequency (RF) waves, electromagnetic radiation, or focused ultrasound waves heating the nanoparticles.

In one embodiment, the IR light can also be simultaneously used as in OCT technology to provide an OCTA image of the retina, or as a nanoparticle-assisted angiogram. The angiogram images can be superimposed, by software, on the OCTA or the OCT to show the exact location of the nanoparticle, e.g., in vessels, or in cysts or cavities, or in the subretinal fluid produced by various diseases of the retina and the choroid. In one embodiment, nanoparticles with a size ranging from 1 nm-8 nm can pass through the smallest breaks of the retinal vessels or retinal pigment epithelium, and be visualized during nanoparticle assisted angiography. This beneficially combines two systems, angiography and OCTA, in one instrument.

In one embodiment, nanoparticles ranging in size from 1 nm-8 nm, or from 8 nm-900 nm generate an internal light after excitation and emit visible light. In this embodiment, the emitted wavelength provides better information from deeper structures, or from the optic nerve head, or in the posterior choroidal circulation, with emission wavelengths appearing akin to stars shining in a dark sky. This emission wavelength can be recorded as a photograph or an angiogram. Because this emitted light is generated internal to a tissue and is not reflected, it does not create interference with incoming invisible IR light. It thus can be seen more distinctly than is possible by standard fluorescein angiography. By selection of the nanoparticle composition, such as quantum dot/plasmonic nanoparticles, one can image the deeper structures located in the choroidal circulation than previously possible with simple OCTA. For example, using nanoparticles from one of the coated functionalized lanthanide series, which then emit visible light and can be visualized and recorded, IR light penetrates deep in the choroid and excites those nanoparticles, which can be visualized and recorded. In one embodiment, the nanoparticles are subjected to wavelength from an IR laser to both heat the nanoparticles and release any medication from the thermosensitive coating, such as chitosan, of a nanoparticle, e.g., anti-VEGF, anticancer drugs, antibiotics, anti-inflammatory agents/inhibitory genes, etc. The wavelength also heats abnormal endothelial cells to enhance the effect of anti-VEGF on the abnormal vessels.

In one embodiment, a known photosensitizer, e.g., verteporphin, is conjugated with antibody coated nanoparticles having a thermosensitive polymeric coating such as chitosan. Upon light activation, the nanoparticles simultaneously release a small amount of photosensitizer from the polymeric coating. Subsequently, after release of the photosensitizer, in the presence of oxygen and laser application, singlet oxygen and free radicals are created. This damages the wall of the abnormal vessels, causing platelet aggregation which closes abnormal vessels, beneficially without damaging normal adjacent tissue or creating a systemic response to the photosensitizer. The inventive method thus is an improvement over and is in contrast to original photodynamic therapy that produced side effects after intravenous injection of a large amount of photosensitizer, such as skin burns when the patient was exposed to sunlight, or an allergic response even as severe as shock or death, or tissue necrosis with photosensitizer extravasation. Nanoparticles produce a fluorescent light upon laser irradiation. This can be simultaneously imaged while the desired tissue is treated and the borders of the neovascular tissue or the lesion becomes visible by the attached antibody coated nanoparticles. It is of note that standard photodynamic therapy for abnormal vessels in ARMD or for neoplasms does not provide any information on the borders of the tumor during therapy. Thus, the investigator has to treat the lesion from the memory and not objectively. This led to many recurrences requiring treatment that unnecessarily damaged the overlaying healthy retina, among other drawbacks. The inventive method solves this problem by allowing visualization of tumor borders and simultaneous release of medication.

In one embodiment, passage of the sized nanoparticles from the circulation provides information on the location and the degree of the damage caused by the disease. Lesions as small as one nm or as large as 900 nm can be imaged. For example, if a damaged area of a vessel exceeds 5 microns, erythrocytes will exit the vessels and cause frank bleeding that obscures the bleeding site. Lesions smaller than 2 microns would allow only non-cellular fluid, i.e., serum, to escape, so this would not be visible by standard OCTA. In contrast, functionalized quantum dot nanoparticles can pass through nanosized openings in the vessels, remain attached to damaged cells, and can be visualized for several hours or days at the site. This permits repeat quantum dot assisted OCTA or angiography over many days, following the lesion during a post-operative period non-invasively using the inventive system.

In one embodiment, since the absorption wavelength of the nanoparticle can be matched with the wavelength generated by OCT, it is possible to excite the nanoparticles to fluoresce. The wavelength of the fluorescent light can be matched with the absorption wavelength of the photosensitizer, e.g. amino-levulinic acid etc., to induce singlet oxygen and free radical formation in a tumor, inducing endothelial cell wall damage of the lesion as many times as needed for therapy. If vessel leakage has persisted and requires re-sealing, this can be accomplished by application of minor thermal laser energy that is absorbed by the nanoparticle and that heats the surrounding area. This is helpful in treating the wet form of age-related macular degeneration, one of the major cause of blindness due to abnormal vessel growth and bleeding under the retina, or diabetic retinopathy with macular edema having early or late stage proliferative retinopathy. Alternatively, in the case of an invisible bleeding site, low level X-ray application can be done. In the presence of an antibody-coated nanoparticle of gold or a gold composite, the functionalized gold nanoparticles enhance the local effect of the radiation while protecting other areas. The same technology can be applied to localized cancers, e.g., breast, prostate, brain, lung, etc. One can also easily repeat treatment, if needed, with a radioactive coating of the antibody-coated quantum dot nanoparticles in cancer patients.

In another embodiment, the nanoparticles may be conjugated with cell penetrating agents such as CPP, ACPP, etc. to a gene/CRISPR cas9 complex that can modify the genetic composition of the cells to which the nanoparticles are targeted. Such a cell may have a genetic abnormality, e.g., age-related macular degeneration etc. and, in this embodiment, the functionalized nanoparticles/genes along with CRISPR cas9 are picked up by the targeted cells, and release the gene into the cell upon or after cellular uptake. As one example, a gene to correct the genetic abnormality in retinitis pigmentosa can allow retinal cells to regain sensitivity to light. As another example, a first conjugated gene is from the opsin family, and a second conjugated gene/CRISPR cas9 complex modifies the genetic composition of cells that might have a genetic abnormality such as retinitis pigmentosa, epilepsy, Alzheimer's disease, Parkinson's disease, etc. As another example, the conjugated gene is an opsin family member such as rhodopsin, halorhodopsin, etc. In another embodiment, the antibody-coated nanoparticle containing the conjugated gene/CRISPR cas9 complex to eliminate the tumor producing gene, or having an inhibitory gene, siRNA, etc. is injected intravenously in an eye or elsewhere as needed. In another embodiment, the antibody-nanoparticle is directed to retinal tumor or brain tumor cells, e.g., retinoblastoma or glioma or glioblastoms. After release of the rhodopsin gene/CRISPR cas9 complex from a thermosensitive coating, one can convert these non-excitable cells to light-sensitive tumor cells that response to light by being depolarized. One can apply non-coagulative pulsed laser fora period of time of about 10 min-15 min or more to the tumor. By applying repeated continuous rapid laser pulses under control of a photoacoustic system, as previously described, using an externally located laser or by a fiber optic, the cell membrane of the tumor cells depolarize. As a result, the tumor is rendered permeable to anticancer or other medication that is released from the coating of the nanoparticle, freely diffusable in the tumor cells to damage the tumor cells.

The tumor can be of neuronal origin such as a glioblastoma in the brain or a retinoblastoma in the eye, or an acoustic neuroma or meningioma, or the tumor may be from the spinal cord cells or peripheral nerves. The tumor can be a melanoma of the choroid or a skin melanoma, or the tumor can be of mesenchymal cells or of ectodermal origin. This technique represents a completely new approach of eliminating the tumor cells without burning them or removing them surgically. By choosing functionalized piezoelectric nanoparticles, one can also use ultrasound or focused ultrasound for both cell depolarization and thermotherapy as needed. Because ultrasound travels deep in tissues, it can be used advantageously in deep body or brain tissues. Nanoparticles are coated with a biocompatible coating such as PEG, CPP, ACPP, etc. or thermosensitive polymers such as chitosan that dissolve during laser therapy and releases a medication, e.g. an anti-VEGF antibody and/or any other medication e.g. anticancer agents melphalan etc. useful to treat a tumor such as a retinoblastoma, glioblastoma, medulloblastoma, acoustic neuroma, spinal cord tumor, peripheral nerve tumor, choroidal melanoma, skin melanoma, mesenchymal cell tumor, tumor of ectodermal origin, basal cell carcinoma, squamous cancer, etc., or an anti-melanoma medication such as allovectin-7, decarbazine, or others such as alkylating agents such as nitrogen mustards including mechlorethamine, cyclophosphamide, melphalan, chlorambucil, ifosfamide and busulfan; nitrosoureas including N-nitroso-N-methylurea (MNU), carmustine (BCNU), lomustine (CCNU) and semustine (MeCCNU), fotemustine and streptozotocin; tetrazines including dacarbazine, mitozolomide and temozolomide; aziridines including thiotepa, mytomycin and diaziquone (AZQ); cisplatin and derivatives including cisplatin, carboplatin, and oxaliplatin; and non-classical alkylating agents including procarbazine and hexamethylmelamine; anti-metabolites such as anti-folates including methotrexate and pemetrexed; fluoropyrimidines including fluorouracil and capecitabine; deoxynucleoside analogues including cytarabine, gemcitabine, decitabine, Vidaza, fludarabine, nelarabine, cladribine, clofarabine and pentostatin; and thiopurines including thioguanine and mercaptopurine; anti-microtubule agents such as vinca alkaloids including vincristine and vinblastine, semi-synthetic vinca alkaloids include vinorelbine, vindesine, and vinflunine; taxanes including paclitaxel and docetaxel; topoisomerase inhibitors including irinotecan, topotecan, etoposide, doxorubicin, mitoxantrone, teniposide, novobiocin, merbarone, and aclarubicin; cytotoxic antibiotics including actinomycin, bleomycin, plicamycin, mitomycin, doxorubicin, daunorubicin, epirubicin, idarubicin, pirarubicin, aclarubicin, and mitoxantrone, etc. to treat melanoma of the choroid or a skin lesion, such as basal cell carcinoma or squamous carcinoma of the skin, etc.

In one embodiment, the antibody coated nanoparticles are coated with an immune checkpoint inhibitor to facilitate leukocyte mediated tumor destruction. Immune checkpoint inhibitors include, but are not limited to, monoclonal antibodies that target either PD-1 or PD-L1 including pembrolizumab (KEYTRUDA®) and nivolumab (OPDIVO®), monoclonal antibodies that target CTLA-4 such as ipilimumab (YERVOY®), and monoclonal antibodies directed against at least one of CD27, CD28, CD40, CD122, CD137, OX40 (also termed CD134), GITR (glucocorticoid-induced TNFR family related gene), ICOS (inducible T-cell costimulatory also termed CD278), A2AR (adenosine A2A receptor), B7-H3 (also termed CD276), B7-H4 (also termed VTCN1), BTLA (B and T lymphocyte attenuator also termed CD272), CTLA-4 (cytotoxic T-lymphocyte-associated protein 4 also termed CD152), IDO (indoleamine 2,3-dioxygenase), KIR (killer-cell immunoglobulin-like receptor), LAG3 (lymphocyte activation gene-3), PD-1 (programmed death 1), PD-L1 (programmed death ligand 1), TIM-3 (T-cell immunoglobulin domain and mucin domain 3), VISTA (V-domain Ig suppressor of T cell activation), and other to be developed.

In one embodiment, the nanoparticles are heated by the same laser that is used to create a fluorescent response, or by another laser producing a wavelength that is absorbed by the nanoparticles to heat them preferentially over the surrounding tissue, e.g., retina or choroid. The nanoparticle temperature is heated to about 43° C., which is below the thermal pain threshold sensation. This heats and thus damages tumor cells by the method previously described in U.S. Pat. No. 8,210,184 which is expressly incorporated by reference herein in its entirety.

In one embodiment, thermotherapy is combined with immune therapy by including the targeted nanoparticles conjugated with immune stimulators, such as modified viral particles or modified plant viral viruses, along with the nanoparticles etc. to induce an immune response to the tumor cells, disease process, Alzheimer's plaques, etc.

In one embodiment, imaging is combined with nanoparticle assisted photoacoustic imaging, OCT, OCTA, FA, focused ultrasound, non-focused ultrasound, MRI, PET scan, CT scan, surface enhanced Raman spectroscopy and imaging, which enhances the molecular diagnosis of a substance attached to the surface of a metallic nanoparticle after it is exposed to the laser light energy as known in the art, etc. recorded to enhance an early disease diagnosis in vivo.

In one embodiment, one can deliver antibiotics, anti-parasitic drugs, anti-fungal drugs, anti-viral drugs anti-inflammatory agents, etc. conjugated with the quantum dot nanoparticles.

The embodiments shown and described in the specification are only specific embodiments of inventors who are skilled in the art and are not limiting in any way to the location in the body, nanoparticle type or composition, disease process, source of energy, medication, gene, etc. Therefore, various changes, modifications, or alterations to those embodiments may be made without departing from the spirit of the invention in the scope of the following claims. The references cited are expressly incorporated by reference herein in their entirety.

What is claimed is:

1. A method for early stage detection and treatment of a pathology in a patient, the method comprising the following steps:
   administering a pathology-specific antibody-coated nanoparticle into a patient's circulation, the pathology-specific antibody-coated nanoparticle comprising a nanoparticle bound to a pathology-specific antibody and further conjugated with an immune checkpoint inhibitor in the form of a monoclonal antibody, wherein the pathology-specific antibody and monoclonal antibody are different,
   allowing a time interval for the pathology-specific antibody of the antibody-coated nanoparticle to attach to a specific antigen in a circulating vesicle or cell,
   thereafter exciting the antibody-coated nanoparticle with an energy source in a retinal vessel in the patient to elicit a nanoparticle-specific wavelength of light response from the antibody-coated nanoparticle attached to the circulating vesicle or cell indicating an early stage pathology in the patient due to the presence of the specific antigen to which the pathology-specific antibody of the antibody-coated nanoparticle is bound,
   imaging and quantifying the nanoparticle-specific wavelength of light response in the retinal vessel in the patient for detection of the early stage pathology prior to a mass associated with the early stage pathology growing beyond a diameter of 3-4 mm and causing a clinical symptom, and
   treating the pathology using the monoclonal antibody so as to facilitate leukocyte mediated destruction, wherein the pathology is cancer.

2. The method of claim 1 where the circulating vesicle or cell originates from a malignant tumor, the method further comprising diagnosing the malignant tumor prior to the malignant tumor having reached a size up to 3 mm in diameter.

3. The method of claim 1 where the nanoparticle is a quantum dot the administering step is by injection; the antigen is at least one of a receptor on a tumor cell membrane, a protein in a blood vessel wall, a sessile tumor, a free circulating tumor cell, an ECV, an infective agent, or an exosome; and the method further comprises applying thermal energy to the antibody-coated nanoparticle attached to the specific antigen in the circulating vesicle or cell, and receiving a photoacoustic sound from the heated antibody-coated nanoparticle attached to the specific antigen in the circulating vesicle or cell to image the circulating vesicle or cell.

4. The method of claim 3 where the nanoparticle has a size ranging from 1 nm-8 nm, 8 nm-20 nm, 20 nm-50 nm, 50 nm-100 nm, 100 nm-500 nm, or 500 nm-900 nm.

5. The method of claim 3 where the imaging and quantifying steps are by fundus photography, nanoparticle assisted angiography, optical coherence tomography (OCT), OCT angiography (OCTA), and combinations thereof.

6. The method of claim 1 where the pathology is at a site selected from the group consisting of retina, choroid, skin, mucosa, and combinations thereof.

7. The method of claim 5 where the imaging and quantifying steps are by OCTA and at least one of a two-dimensional and a three dimensional image of the antibody-coated nanoparticle is provided.

8. The method of claim 1 where the antibody-coated nanoparticle contains an additional coating.

9. The method of claim 8 where the additional coating is selected from the group consisting of a polymer, a thermosensitive polymer, chitosan, a cell penetrating agent, a part of a biotin/streptavadin binding pair, an antibody, an antigen, and combinations thereof.

10. The method of claim 9 where the additional coating is a thermosensitive polymer, and a photosensitizer is conjugated to the thermosensitive polymer.

11. The method of claim 3 where the antibody-coated nanoparticle is conjugated to a gene that can modify the genetic composition of the circulating vesicle or cell to which the antibody: coated nanoparticle is attached.

12. The method of claim 3 where the antibody-coated nanoparticle further comprises a thermosensitive coating and an anticancer agent, and the method further comprises applying repeated non-coagulative laser pulses for about 10 min-15 min controlled by a photoacoustic system using an externally located laser or a fiber optic to increase a temperature of the circulating vesicle or cell to 42° C. to 43° C. to depolarize the circulating vesicle or cell, release the anticancer agent to the circulating vesicle or cell, render the circulating vesicle or cell membrane permeable to the anti-cancer agent that is released from the thermosensitive coating of the antibody-coated nanoparticle to freely diffuse the anti-cancer agent in the circulating vesicle or cell to damage the circulating vesicle or cell.

13. The method of claim 12 where the cancer is a glioblastoma, a retinoblastoma, a medulloblastoma, an acoustic neuroma, a spinal cord tumor, a peripheral nerve tumor, a choroidal melanoma, a skin melanoma, a mesenchymal cell tumor, a tumor of ectodermal origin, a basal cell carcinoma, a squamous cancer, and combinations thereof.

14. The method of claim 12 where the anticancer agent is selected from the group consisting of melphalan, decarbazine, 5-fluorouracil, mechlorethamine, cyclophosphamide, melphalan, chlorambucil, ifosfamide, busulfan, N-nitroso-N-methylurea (MNU), carmustine (BCNU), lomustine (CCNU), semustine (MeCCNU), fotemustine, streptozotocin, dacarbazine, mitozolomide, temozolomide, thiotepa, mytomycin, diaziquone (AZQ), cisplatin, carboplatin, oxaliplatin, procarbazine, hexamethylmelamine, methotrexate, pemetrexed, fluorouracil, capecitabine, cytarabine, gemcitabine, decitabine, azacitidine, fludarabine, nelarabine, cladribine, clofarabine, pentostatin, thioguanine, mercaptopurine, vincristine, vinblastine, vinorelbine, vindesine, vinflunine, paclitaxel, docetaxel, irinotecan, topotecan, etoposide, doxorubicin, mitoxantrone, teniposide, novobiocin, merbarone, aclarubicin, actinomycin, bleomycin, plicamycin, mitomycin, doxorubicin, daunorubicin, epirubicin, idarubicin, pirarubicin, aclarubicin, mitoxantrone, and combinations thereof.

15. The method of claim 1 further comprising analyzing a blood sample from the patient for a component selected from the group consisting of a biomarker, a tumor protein, a microDNA, a microRNA, an enzyme, a nucleosome, an extracellular vesicle, a free floating tumor cell, a biomolecule, and combinations thereof.

16. The method of claim 1 where the imaging step uses a method selected from the group consisting of antibody-coated nanoparticle assisted photoacoustic technology, ultrasound, surface enhanced Raman spectroscopy, nanoparticle assisted fluorescence angiography, photography, computed tomography, magnetic resonance imaging, and combinations thereof.

17. The method of claim 1 where the antibody-coated nanoparticle is further coated with an immune stimulator in the form of modified viral particles or modified plant viruses, and where the method further comprises treating the pathology using the modified viral particles or modified plant viruses to induce an immune response to tumor cells.

18. A recognition and treatment method for an early stage of a tumor without producing a clinical symptom in a patient, the method comprising:
  defining a change in a tissue of a patient, the change indicating an early stage lesion in at least one cell in the tissue,
  administering a plurality of nanoparticles to the patient, where the nanoparticles are bound to an a lesion-specific antibody against a protein in the lesion and are coated with a thermosensitive polymer containing an immune checkpoint inhibitor in the form of a monoclonal antibody for therapy of the lesion, wherein the lesion-specific antibody and monoclonal antibody are different,
  interrogating the cellular and extracellular vesicles in the patient's blood using a photoacoustic spectroscopic system and an optical spectroscopic fundus camera equipped with a laser that is focused on a retinal vessel of the patient,
  recording, imaging, quantifying, and/or analyzing the patient's cells and extracellular vesicles according to the nanoparticles in the retinal vessel in the patient,
  treating the lesion using the immune checkpoint inhibitor so as to facilitate leukocyte mediated tumor destruction, and
  using the system to increase the temperature of the nanoparticles to a temperature of 42° C. to 43° C. to release the monoclonal antibody from the thermosensitive polymer to treat the lesion.

19. The method of claim 18 further comprising exposing the nanoparticles to a thermal energy source from a thermal energy delivery unit controlled by the photoacoustic spectroscopic system to increase the temperature in the nanoparticles, resulting in a photoacoustic sound that is recorded by the photoacoustic spectroscopic system, the method combining photoacoustic imaging to verify and image the location of the early stage lesion.

20. The method of claim 19 where the photoacoustic spectroscopic system controls the amount of thermal energy to maintain a system operator desired temperature ranging from 38° C. to 45° C.

21. The method of claim 18 where the nanoparticles are selected from the group consisting of quantum dots, organic, inorganic, synthetic, magnetic, paramagnetic, non-magnetic, nano/microbubble, piezoelectric, shell structure, cage structure, wire structure, tube structure, spherical, cylindroid, tube, multi-faceted, gold, silica, iron, iron oxide, zinc, zinc oxide or their composites, cadmium sulfate, lanthanide, upconverting nanoparticles, copper core or surface, nickel core or surface, carbon core or surface, graphene core or surface, radioactive surface, and combinations thereof.

22. The method of claim 18 further comprising stimulating the nanoparticles using a light source, and imaging the nanoparticles using optical coherence tomography angiography (OCTA) so as to determine the location of the lesion.

* * * * *